United States Patent [19]

Benco et al.

[11] Patent Number: 5,554,272
[45] Date of Patent: Sep. 10, 1996

[54] PLANAR BICARBONATE SENSOR

[75] Inventors: John S. Benco, Holliston; Joseph S. Foos, Needham, both of Mass.

[73] Assignee: Ciba Corning Diagnostics Corp., Medfield, Mass.

[21] Appl. No.: 513,266

[22] Filed: Aug. 10, 1995

[51] Int. Cl.$^6$ .................................................. G01N 27/26
[52] U.S. Cl. .................. 205/782.5; 205/783; 205/785.5; 205/792; 204/418; 204/416; 204/415; 204/406; 204/403; 204/433; 204/435; 422/68.1; 422/82.01; 422/82.02; 422/82.03; 422/82.04
[58] Field of Search ................................ 205/782.5, 783, 205/785.5, 792; 204/418, 416, 415, 406, 403, 433, 435; 422/68.1, 82.01, 82.02, 82.03, 82.04

[56] References Cited

U.S. PATENT DOCUMENTS

| | | | |
|---|---|---|---|
| 3,705,088 | 12/1972 | Niedrach et al. | 204/195 |
| 3,896,020 | 7/1975 | Le Blanc, Jr. | 204/195 |
| 3,898,147 | 8/1975 | Niedrach | 204/195 |
| 4,534,355 | 8/1985 | Potter | 204/403 |
| 4,536,274 | 8/1985 | Papadakis et al. | 204/433 |
| 4,571,292 | 2/1986 | Liu et al. | 204/412 |
| 4,734,184 | 3/1988 | Burleigh et al. | 204/409 |
| 4,818,361 | 4/1989 | Burgess et al. | 204/406 |
| 4,839,020 | 6/1989 | Yamaguchi et al. | 204/424 |
| 5,110,441 | 5/1992 | Kinlen et al. | 204/418 |
| 5,174,872 | 12/1992 | Scott | 204/416 |
| 5,304,293 | 4/1994 | Tierney et al. | 204/415 |
| 5,336,388 | 8/1994 | Leader et al. | 204/418 |

FOREIGN PATENT DOCUMENTS

| | | |
|---|---|---|
| 0625704 | 11/1994 | European Pat. Off. . |
| 93/13411 | 7/1993 | WIPO . |

OTHER PUBLICATIONS

Botre, F., et al, "A Potentiometric Ion Selective Bicarbonate Electrode Based on a Liquid Exchanger Membrane", (Fac. Farm., Univ. La Sapienza), Carbonic Anhydrase, Proc. Int. Workshop 1990 (Pub. 1991) pp. 322–326 no month available.

Coon, R. L., et al. "Evaluation of a Dual–Function pH and Pco$_2$ in vivo Sensor", *J. of Applied Physiology*, vol. 40, No. 4, pp. 625–629 (April 1976).

Covington, A. K., ed., *Ion Selective Electrode Methodology*, vol. 1, CRC Press, Inc., pp. 32–33 (1979) no month available.

Funck, Robert J. J., et al., "Bicarbonate–Sensitive Liquid Membrane Electrodes Based on Neutral Carriers for Hydrogen Ions", *Anal. Chem.* vol. 54, pp. 423–429 (1982) no month available.

Glab, S., et al., "Metal–Metal Oxide and Metal Oxide Electrodes as pH Sensors," *Critical Reviews in Analytical Chemistry*, vol. 21, pp. 29–47 (1989) no month available.

Grekovich, A. L., et al., "Bicarbonate Electrode on the Basis of Solid and Liquid Ion–Exchange Membranes", A. A. Zhdanov Leningrad State University. Translated from Zhurnal Analiticheskoi Khimii, vol. 28, No. 6, pp. 1206–1209, Jun. 1973. UDC 543.257: 543.544, Consultants Bureau, a division of Plenum Publishing Corporation, 227 West 17th Street, New York, New York, pp. 1069–1072.

(List continued on next page.)

*Primary Examiner*—Bruce F. Bell
*Attorney, Agent, or Firm*—Judith A. Roesler; Arthur S. Morgenstern

[57] ABSTRACT

A planar bicarbonate sensor has been discovered that has a dried residue internal electrolyte layer comprising a bicarbonate source and a halide salt of potassium, lithium, or sodium. The flow-through sensor is capable of providing bicarbonate level of a liquid sample, and when coupled with a pH sensor, may be used to determine the partial carbon dioxide level in the sample. The sensor provides many commercially desirable characteristics including an adequate lifetime, good response time, and good stability upon first usage.

7 Claims, 5 Drawing Sheets

OTHER PUBLICATIONS

Grubb, W. T., et al., "Palladium–Palladium Oxide pH Electrodes", *Anal. Chem.*, vol. 52, No. 2, pp. 270–273 (1980) no month available.

Kinoshita, Eita, et al., "An Examination of the Palladium/Palladium Oxide System and its utility for pH Sensing Electrodes", *Electrochimica Acta*, vol. 31, No. 1, pp. 29–38 (1986) no month available.

Liu, C–C. et al., "A Palladium–Palladium Oxide Miniature pH Electrode", *Science*, vol. 207, No. 11, pp. 188–189 (1980) no month available.

Meyerhoff, Mark E., "New In Vitro Analytical Approaches for Clinical Chemistry Measurements in Critical Care", *Clin. Chem.*, vol. 36, No. 8(B), pp. 1567–1572 (1990) no month available.

Mostert, I. A., et al., "Optimization of a Bicarbonate–Selective Liquid Membrane Electrode", *Mikrochim Acta*, vol. 3, No. 5–6, pp. 425–432 (1984) no month available.

Oesch, Urs, et al., "Bicarbonate–Sensitive Electrode Based on Planar Thin Membrane Technology", *Anal. Chem.*, vol. 59, pp. 2131–2135 (1987) no month available.

Oubda, S. T., et al., "Thin Film IRO2–Electrodes Modified by Pt–Nucleation Processes: Their Application for Construction of a pH and Glucose Sensor," Extended Abstracts of the Spring Meeting of the ECS, Honolulu, 93–1, Abstract No., 1705, pp. 2332–2333 (1993) no month available.

Pedigo, J. L., et al., "A Printer's Primer," *Hybrid Circuit Technology*, pp. 28–31, (Feb. 1992).

Rao, Xiaohong, et al., "A Novel Combinational pH–$Pco_2$ Microelectrode", *Anal. Biochem.* vol. 212, pp. 43–46 (1993) no month available.

Telting–Diaz, M. et al., "Simplified Dual–Lumen Catheter Design for Simultaneous Potentiometric Monitoring of Carbon Dioxide and pH", *Anal. Chem.*, vol. 66, pp. 576–583 (1994) no month available.

Ushizawa, N. et al., "Electrode for Bicarbonate Ion Determination in Blood", *CA Selects: Analytical Electrochemistry*, Issue 4, Abstract No. 118:55588h (1993) no month available.

Wang, Enju, "Development of Bicarbonate— and Carbonate–Selective Flow–Through Eelctrodes and Their Applications in Blood Serum", Swiss Federal Institute of Technology, Zurich (1989) no month available.

Yim, Hyoung–Sik, et al., "Polymer Membrane–Based Ion–, Gas— and Bio–selective Potentiometric Sensors", *Biosensors & Bioelectronics*, vol. 8, pp. 1–38 (1993) no month available.

PLANAR BICARBONATE SENSOR

FIELD OF THE INVENTION

This invention relates to a planar sensors useful for the measurement of bicarbonate. The sensors may also be utilized for measurement of partial carbon dioxide when used in combination with a pH sensor.

BACKGROUND

Planar format sensors have generally been described in the literature and are considered advantageous over three-dimensional sensors under many circumstances. The planar format typically comprises relatively thin layers of materials which are applied to a substrate base using thick-film or thin-film techniques, including, for example, silk-screen printing. Planar sensors are typically smaller than three-dimensional sensors and therefor the sensing instrument itself may be scaled down. Additionally the planar sensor is easily and inexpensively manufactured and simple to operate.

In preparing planar format sensors, performance issues must be addressed and remedied before commercializing the sensor. Problems associated with preparing a commercially acceptable bicarbonate sensor include, for example, inadequate lifetime of the sensor, slow response time of the sensor, and extended time frame required before the sensor reaches a stable potential upon the sensors first usage.

Planar bicarbonate sensors that offer an improved response with respect to the at least one of the above-enumerated problems are needed.

SUMMARY OF INVENTION

The above-described problem has been solved with the discovery of a planar bicarbonate sensor comprising an electrically nonconductive substrate having applied thereto in a planar format an electrically conductive material in at least one region adjacent to said substrate; a dielectric coating covering at least a lead portion of said electrically conductive material but leaving exposed at least an electrode area of said electrically conductive material and leaving exposed at least a contact area on said region of said electrically conductive material; a silver/silver halide transducer present adjacent to said electrically conductive material in said exposed electrode area; an internal electrolyte layer present on top of and adjacent to said transducer; a cover membrane present on top of and adjacent to said internal electrolyte layer, wherein said dried internal electrolyte is prepared from an aqueous solution comprising of from about 0.0002 M to about 0.0003 M of a bicarbonate source, a halide salt of potassium, lithium, or sodium.

A method of preparing a bicarbonate sensor has also been discovered, said method comprising selecting a substrate; applying an electrically conductive region on at least a portion of said substrate; coating said electrically conductive region with a dielectric but leaving exposed a transducer region on said electrically conductive region and a contact region on said electrically conductive region; forming a silver/silver halide layer on said transducer region to form a transducer; forming an internal electrolyte dried residue layer having a dried thickness of from about 2.5 µm to about 4 µm thickness on at least said transducer portion of said sensor wherein said internal electrolyte layer is prepared from an aqueous solution comprising a bicarbonate source in an amount ranging from about 0.0002 M to about 0.0003 M, a halide salt of potassium, lithium, sodium; and forming on top of and adjacent to at least said dried internal electrolyte layer a cover membrane layer having a thickness of from about 20 to about 60 µm by forming a solution comprising an organic solvent, a gas permeable polymeric or copolymeric material, a proton selective ionophore, a plasticizer, and a lipophilic salt present in an amount ranging form about 0.1 wt./vol. % to about 0.5 wt./vol. % and then drying said solution to form said cover membrane layer.

Also provided is a method of measuring a bicarbonate level in a liquid sample, the method comprising contacting a liquid sample with a planar bicarbonate sensor as described above and with a reference electrode either directly or indirectly, connecting said exposed contact area of said sensor with a sensing instrument, providing an electrical current from said sensing instrument through said reference and said contact area, and measuring an electrical signal provided by said pH sensing instrument.

Also provided is a method of measuring a partial $CO_2$ level in a biological sample, the method comprising contacting a liquid sample with said planar bicarbonate sensor described above, a reference electrode, and a pH sensor; connecting contact areas of said bicarbonate sensor and said pH sensor with a sensing instrument; connecting said reference electrode with said sensing instrument; providing an electrical current from said sensing instrument through said reference electrode and said contact areas of said sensors; measuring an electrical signal from said bicarbonate sensor to provide a bicarbonate reading on said sensing instrument; measuring an electrical signal from said pH signal from said pH sensor to provide a pH reading on said sensing instrument; and subtracting said bicarbonate reading from said pH reading to provide a $pCO_2$ reading on said instrument.

The invention provides an economical planar bicarbonate sensor capable of accurate measurement of bicarbonate concentration. The sensor may also be used in the measurement of the partial pressure of carbon dioxide ($pCO_2$) and provides an acceptable precision and accuracy. Another advantage of the present invention is that the internal electrolyte of the sensor is a dried residue such that the electrolyte does not have to be maintained in a hydrated state.

DETAILED DESCRIPTION

The invention is suitable for use in determining the concentration of bicarbonate ($HCO_3^-$) and optionally the partial pressure of carbon dioxide ($pCO_2$) of liquid samples, particularly biological fluids. Non-liquid samples may be prepared as liquid samples and thereafter tested by techniques known to those skilled in the art. Whole blood may be directly tested using the inventive sensor without requiring additional manipulation of the sample, e.g. dilution.

According to the invention, the bicarbonate sensor 5 is fabricated on an electrically nonconductive substrate base support 10. Materials that may be used as the base support are well-known and include, for example, ceramic, glass, refractory, and polymeric materials, combinations thereof, and so on. Currently, substrates of an alumina and glass binder combination are favored. If desired, grooves and/or holes may be fashioned in the nonconductive substrate such that layers can be specifically applied to sections on the substrate. Additionally, the substrates may be perforated or otherwise divided such that many electrodes may be prepared simultaneously on the substrate during the manufacturing of the planar electrodes thus providing a low cost method of production.

A transducer 15 region provides the active portion of the electrode of the sensor. Materials that may be used to form the transducer region preferably comprise a silver/silver halide material (most preferably a Ag/AgCl) and equivalents thereof. The transducer is applied adjacent to and on top of a portion of an electrically conductive region 16 by any suitable technique, including electrochemical plating and thick or thin film technology, and so on. The electrically conductive region 16, 17, 20, and 25 is prepared from a suitable electrically conductive material which may be applied adjacent to the substrate in various known ways. In a preferred embodiment, the electrically conductive region is prepared as two contiguous regions 16, 17 and 20, 25, with the first region 16, 17 prepared from a material comprising silver and the second region 20, 25 comprising gold. Most preferably, the transducer 15 is applied on top of a portion of the first region 16 thus forming Ag/AgCl on top of a silver based material. With the exception of an exposed transducer region 15, 16 and an exposed contact region 25 of the electrically conductive region, at least the lead portion of the sensor 17, 20 is covered by a dielectric insulating material 26, as is well-known to those skilled in the art. As a matter of convenience in fabricating the sensor, it is preferred that the entire sensor is subjected to the dielectric coating with the exception of the exposed transducer region and the exposed contact region.

An internal electrolyte 27 is superimposed directly on top of at least the transducer region 15, and the adjacent portion of the electrically conductive region 16 of the sensor. The internal electrolyte may be advantageously prepared as a dried residue comprising a bicarbonate source and a halide salt of potassium, lithium or sodium, mixtures thereof, and equivalents thereof. Typically, substantially equal amounts of the bicarbonate source and the halide salt of potassium, lithium, or sodium may be used, although this may be varied as desired. It has been found that the level of the bicarbonate source is related to extending the lifetime of the sensor. Maximum lifetime of the sensor may be realized using from about 0.0002 M to about 0.0003 M of the bicarbonate source. Although the bicarbonate source may be used outside this range, the resultant sensor has been observed to more quickly degrade over time. The lifetime of the sensors is highly variable depending upon many variables, but particularly preferred sensors have a lifetime of at least about 7 days, and more preferred sensors have a lifetime of at least about 30 days, as exhibited by no more than about −2.5 mV/dec deterioration in the sensor slope over the given period of usage.

In fabricating the electrode, the internal electrolyte residue is preferably prepared from an aqueous solution containing the bicarbonate source and the salt of the potassium, lithium or sodium. Preferably the aqueous solution contains suitable materials for forming a dried residue layer including, for example, polyvinyl alcohol, polyHEMA, gelatin, dextran, hydrogels or equivalents thereof. In a preferred embodiment the bicarbonate and salt are present in an aqueous solution of from about 0.1 to about 5 wt./vol. % (most preferably about 0.5 wt./vol. %) of polyvinyl alcohol, with said percentages based on the wt./vol. of the total solution. Most preferably, an aqueous solution of about 0.5 wt./vol. % polyvinyl alcohol is combined with sodium bicarbonate (preferably about 0.0002 M) potassium chloride (preferably about 0.0002 M) and applied to the entire substrate, with the exception of the exposed contact region, thus forming the internal electrolyte. Once applied, the internal electrolyte layer is then dried to form a residue. The internal electrolyte residue may be hydrated during normal usage with the sample or by any other known method.

The cover membrane 36 of the sensor is applied directly on top of the dried internal electrolyte residue 27. The cover membrane may be conveniently prepared from a solution (preferably a non-aqueous solution) of water permeable and gas permeable polymeric materials known for membrane formation to those skilled in the art. Preferably an lipophilic salt (or combinations thereof) is included in the cover membrane solution, with appropriate lipophilic salts such as those listed in the 1991 Fluka Chemika-Selectophore Catalog (page 46, 1991, hereby incorporated by reference). A particularly useful solution for preparation of the cover membrane comprises an organic solvent (preferably tetrahydrofuran, with a solid to solvent ratio of about 10% wt./vol.), a proton selective ionophore (preferably tridodecylamine in an amount from about 3 to about 1 wt. %, more preferably about 2 wt. %), a polyvinyl halide type of polymeric or copolymeric material (preferably polyvinyl chloride present in an amount from about 25 to about 35 wt. %, more preferably about 28.6 wt. %), a plasticizer (preferably a dioctyl phthalate present in an amount ranging from about 65 to 75 wt. %, most preferably about 69 wt. %) and a lipophilic salt {preferably a potassium-tetra (p-chloro phenyl) borate} present in an amount ranging from about 0.01 to about 2 wt. %, more preferably from about 0.1 to about 0.5 wt. %), and equivalents thereof, with said percentages based on the wt./vol. of the total cover membrane solution. Unexpectedly, it has been found that sensors exhibiting a minimal drift on first usage may be prepared when the lipophilic salt is utilized in a range of from about 0.1 to about 0.5 wt. %, most preferably about 0.4 wt. %. The minimal drift is defined as less than or equal to about 0.025 mV/min. drift at one hour on first usage.

The cover membrane solution may be applied on top of the internal electrolyte by any appropriate method known to those skilled in the art, including dip coating and solvent casting. The solution is then allowed to evaporate and a dried residue is left to form the active cover membrane. Alternatively, a pre-formed cover membrane may be applied on the sensor by techniques known to those skilled in the art.

According to the invention, the presence of the internal electrolyte contributes to the response time of the sensor, particularly when the cover membrane and internal electrolyte are of a particular thickness. It has been discovered that the thickness of the internal electrolyte acts to offset the typical negative characteristics of a thicker cover membrane (i.e. slow response time). Unexpectedly, the inventive sensor exhibits a fast response time in addition to a satisfactory lifetime, as achieved by manipulating the dry residue thickness of the internal electrolyte and cover membrane layers. The internal electrolyte preferably has a thickness of from about 3 μm to about 4 μm and the cover membrane should have a thickness of from about 20 μm to about 60 μm. More preferably the internal electrolyte is prepared to have a thickness ranging from 2.5 to 4 μm (most preferably about 3.4 μm) and the cover membrane has a thickness ranging from 20 μm to 60 μm (more preferably 40 μm to 50 μm and most preferably about 48.2 μm). Unexpectedly, when the internal electrolyte and cover membrane layers are prepared within these ranges, the response time of the sensors may be about 95% at 2 seconds (comparing sensor output at 30 seconds with sensor output at 2 minutes). It is within the knowledge of one skilled in the art to prepare the layers within these ranges using known methods.

Components described herein, as well as additional features, may be arranged in the planar format on non-conductive substrates in various configurations. For example, as shown in the FIG. 1, a bicarbonate sensor 5 is prepared using an electrically nonconductive substrate 10 having present thereon an electrically conductive material having a first region 16 and 17 (preferably a silver based material) and a second region 20, 25 (preferably a gold based material) adheringly applied adjacent to the substrate 10. An insulating dielectric coating 26 is applied over the substrate and electrically conductive lead portion 17 and 20 but not over an exposed transducer area 15 and an exposed contact area 25. In the exposed transducer area 15, the silver/silver halide material 15 is applied. The exposed contact area 25 is where electrical contact may be made between the sensor 5 and the bicarbonate sensing instrument. The sensor has been found to be particularly useful as a flow-through electrode.

Figure 2:
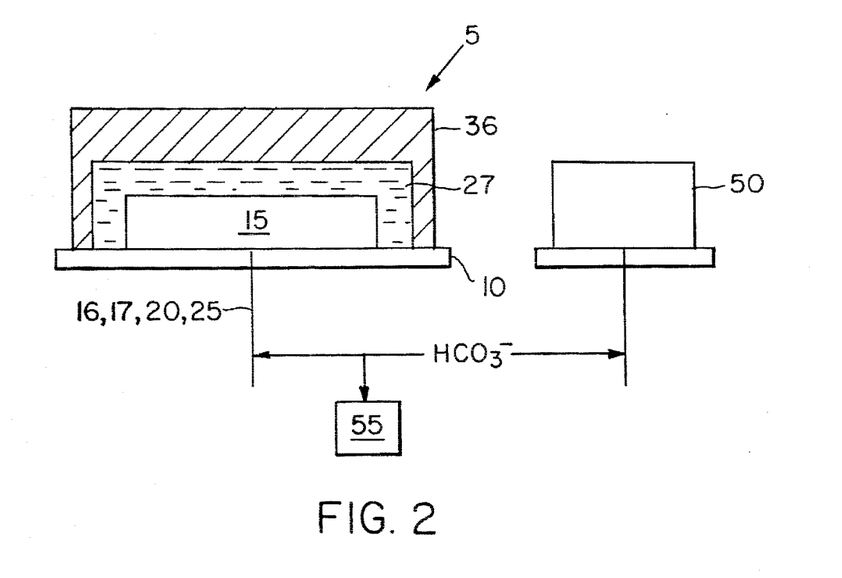
FIG. 2 is a side view of a single electrode, where the various planar layers are shown.

FIG. 2 illustrates how the internal electrolyte 27 may be superimposed over the transducer 15 and how the cover membrane 36 is superimposed over the internal electrolyte layer 27. As shown, the sensor 5 is connected to a reference electrode 50 and sensing instrumentation 55 thereby yielding a bicarbonate measurement.

Figure 3:
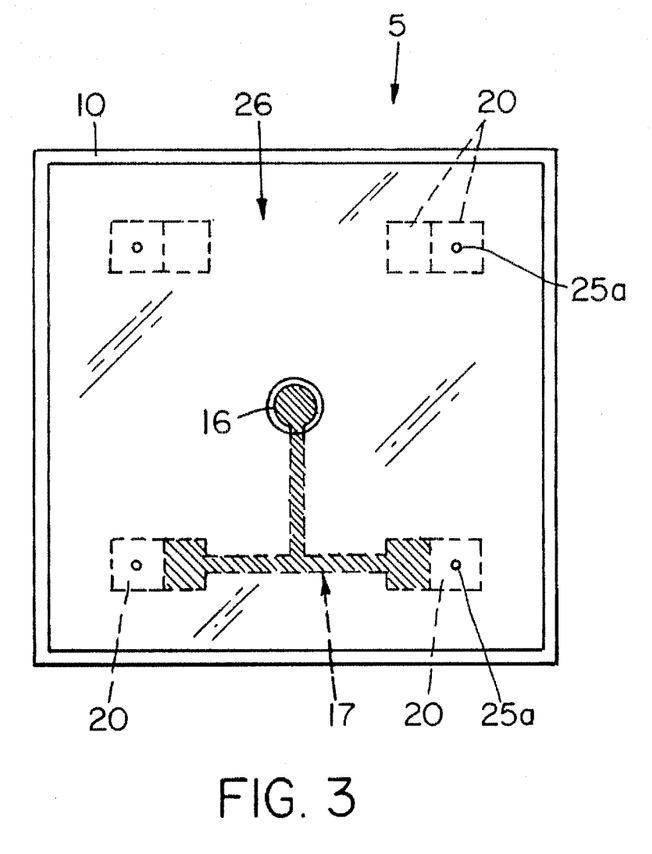
FIG. 3 is a front view of a single planar substrate, as used in Example 7.
Figure 3A:
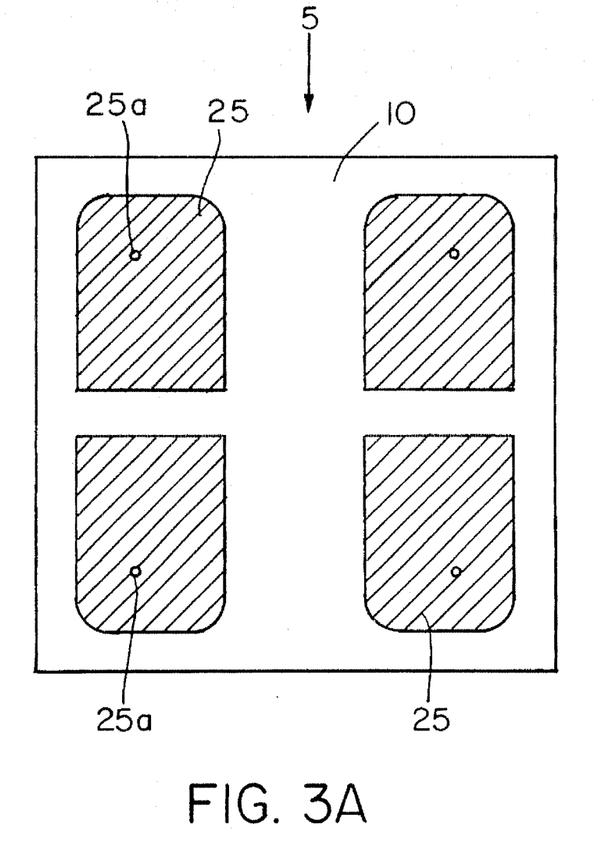
FIG. 3a is a back view of the single planar substrate shown in FIG. 3.

FIGS. 3 (front) and 3a (back) show a bicarbonate sensor 5 having openings (holes) 25a present through the substrate 10. The exposed electrically conductive regions 25 extend through the openings 25a such that contact is made from the exposed electrically conductive regions of the back of the sensor 25 to the front of the sensor and the electrically conductive lead portions 20 that are covered by the insulating dielectric coating 26. At least one of the exposed electrically conductive regions on the back of the sensor 25 are thus connected to the electrically conductive lead portion 17 and 20 and the exposed transducer area 16 at the front of the sensor.

Typically, a potential reading of the sample is obtained between the bicarbonate electrode and a suitable reference electrode (such as for example, a silver/silver halide reference electrode). The bicarbonate sensor may also be used in a sensor system that provides a mechanism for responding to the pH of the sample thus providing a system for measuring the concentration of the partial pressure of carbon dioxide ($CO_2$) present in the liquid sample by various known techniques.

More particularly, for example, in a bicarbonate sensor, where the potential of the system responds to the change of the pH of the sample ($H^+_s$) and the change of pH in the internal electrolyte due to the carbon dioxide in the sample ($H^+_i$), the responses can be modeled as a Nernstian function such that:

$$\Delta\xi = (RT/F)\log([H^+_s]/[H^+_i]). \quad [1]$$

Since the internal electrolyte of the bicarbonate electrode has a fixed concentration of bicarbonate ions, the equation may be converted into the following via the known equilibrium:

$$K = ([H^+_i][HCO_3^-]/K_a pCO_2 \quad [2]$$

where:

$$[HCO_3^-] = \text{constant} = K' \quad [3]$$

then rewriting equation [2]

$$KK_a pCO_2/K' = [H^{30}_i] \text{ or } K''pCO_2 = [H^+_i] \quad [4]$$

thus substituting, equation [1] then becomes:

$$\Delta\xi = (RT/F)\log([H^+_s]/pCO_2) - \log K'' \quad [5]$$

and by combining the following calculation may be completed.

$$\Delta\xi = (RT/F)\log([H^+_s]/pCO_2) \quad [6]$$

The sensor responds to the proton concentration and the partial $CO_2$ pressure of the sample. These two parameters of the solution sample may then be related to the bicarbonate concentration according to the Henderson-Hasselbach equation as known in the art. Thus, reforming the Henderson-Hasselbach equation and taking logs gives:

$$-\log[HCO_3^-] + \log KK_s = \log([H_s^+]/pCO_2) \quad [7]$$

$$\Delta\xi'' = -(RT/F)\log([HCO_3^-]). \quad [8]$$

The pH of the sample may be measured in terms of a mV output using a separate pH electrode versus a reference and the bicarbonate concentration is measured in terms of a mV output using the inventive bicarbonate electrode versus a reference (either directly or indirectly). Mathematical subtraction of the pH mV minus the $HCO_3^-$ mV yields $pCO_2$ mV, as shown in the following calculations.

Where the pH sensor output is:

$$\Delta\xi_{pH} = (RT/F)\log[H^+_s] \quad [9]$$

and the equation [9] minus equations [6], from above, yields $$\Delta\xi''' = (RT/F)\log pCO_2. \quad [10]$$

The output linearly related to the log of $pCO_2$ is provided by equation [10], which has a theoretical slope of 59.16 mV/dec at 25° C. Any other method known in the art may be employed to obtain a subtracted output and is not limited to the above example. Such a method could be, for example, an analog subtraction using an operational amplifier. An instrument incorporating the bicarbonate sensor may provide a bicarbonate reading and a pH reading and a $pCO_2$ reading calculated from the bicarbonate and pH readings, or alternatively, the instrument may only show a $pCO_2$ reading already calculated from output from a pH electrode and a bicarbonate electrode.

Although the electrical circuitry may be varied, a particularly useful circuitry for the measurement of $pCO_2$ may generate a $pCO_2$ signal by the following system. In a preferred circuitry, a first differential signal means is connected to the exposed contact region of the pH sensor and a reference signal and generates a first potential differential signal between the pH sensor and the reference signal. A second differential signal means is connected to the exposed contact region of the bicarbonate sensor and the reference signal and generates a second potential differential between the bicarbonate sensor and the reference signal. The reference signal is generated from a third differential signal means that is connected to a ground electrode and a reference electrode. A mathematical subtraction of the first differential signal minus the second differential signal yields a $pCO_2$ signal.

It is to be understood that various modifications to the invention will be apparent to and can readily be made by those skilled in the art, given the disclosure herein, without departing from the scope and materials of this invention. It is not, however, intended that the scope of the claims appended hereto be limited to the description as set forth herein, but rather that the claims be construed as encompassing all features of patentable novelty which reside in the present invention, including all features which would be treated as equivalents thereof by those skilled in the art to which the invention pertains. It is also noted that the examples given herein are intended to illustrate and not to limit the invention.

EXAMPLE 1

The electrical circuitry utilized for the Examples 1–6 is described in *Ion-Selective Electrode Methodology*, Vol. I, Ed. Arthur K. Covington, CRC Press, 1979, pp. 32–33. (hereby incorporated by reference).

Figure 1:
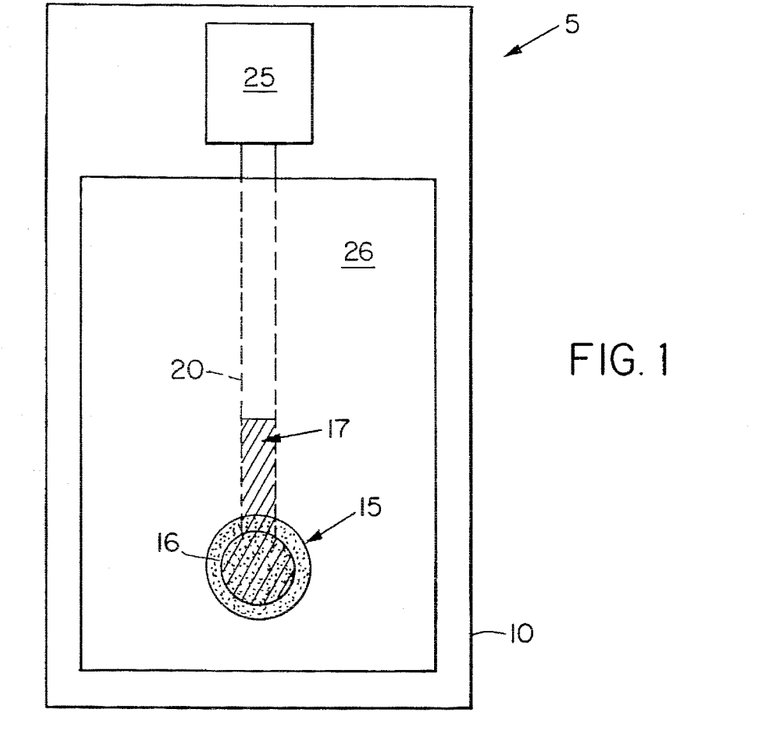
FIG. 1 is a top view of a single planar substrate, as used in Examples 1–6.

The substrate chips upon which each type of planar sensors were fabricated were 2" by 2" wafers perforated to form a total of 40 sensors. The wafers were made of approximately 96% alumina and approximately 4% glass binder, as purchased from Coors Ceramic Company, Grand Junction, Colo. As shown in FIG. 1, a electrically conductive strip was applied where a gold strip was applied in a first region 20, 25 and a silver strip was applied in a second region 16, 17. The gold was purchased from E.I. DuPont DeNemours & Company of Wilmington, Del. Upon depositing the conductive regions on the substrate chips 10, the chips were heated at 850° C. for 6 minutes. A dielectric insulating material 26 (Cat. No. 9615 from E.I. DuPont DeNemours & Co.) was applied over the substrate and conductive regions with the exception of exposed portions 16 and 25. The chips were then reheated at 850° C. for 6 minutes.

On the substrate in the transducer region 16, 0.1 M KCl solution was electrochemically plated at −1.2 mA for 2.5 minutes, thus forming the Ag/AgCl transducer 15. The internal electrolyte solution was prepared with a 0.5 wt. % aqueous solution of 100% hydrolyzed polyvinyl alcohol having present about 0.0002 M of chloride ions and about 0.0002 M sodium bicarbonate ions. The resulting dried residue contained approximately 40 mM of chloride ions and approximately 40 mM of sodium bicarbonate ions. Approximately 1.2 ml of the internal electrolyte solution was applied to the wafer and the water evaporated to form the dry residue of the internal electrolyte having a thickness of approximately 3.4 µm.

The cover membrane solution was prepared as a 10 wt. % solution of solids in tetrahydrofuran (THF), with the solids selected as follows: approx. 69 wt. % dioctyl phthalate (DOP); approx. 28.2 wt. % polyvinyl chloride (PVC); approx. 2.1 wt. % tridodecylamine (TDDA); and approx. 0.7 wt. % potassium-tetra(p-chloro phenyl)borate (KtpClPB), with said wt. % based on the total weight of solids in the solution. About 1.3 ml of this solution was applied to the wafer on top of the dried residue of the internal electrolyte layer. Once the solvent was allowed to evaporate the cover membrane was formed. The formed cover membrane had a thickness of about 48.2 µm. Thereafter the polymeric layers were cut and the wafer divided as per the perforation of the substrate wafer to provide 40 bicarbonate electrodes.

EXAMPLE 2

The planar bicarbonate sensor prepared as described in EXAMPLE 1 was tested along with a commercially available Ciba-Corning 200 series pH electrode (three-dimensional) and a commercially available Ciba Corning 200 Series Severinghaus $pCO_2$ sensor (three-dimensional). Within the same sample path was a commercially available Ciba Corning 200 Series reference electrode. All sensors were tested in the same sample path. The planar bicarbonate sensor was placed into an appropriate holding apparatus to facilitate measurements.

Figure 5:
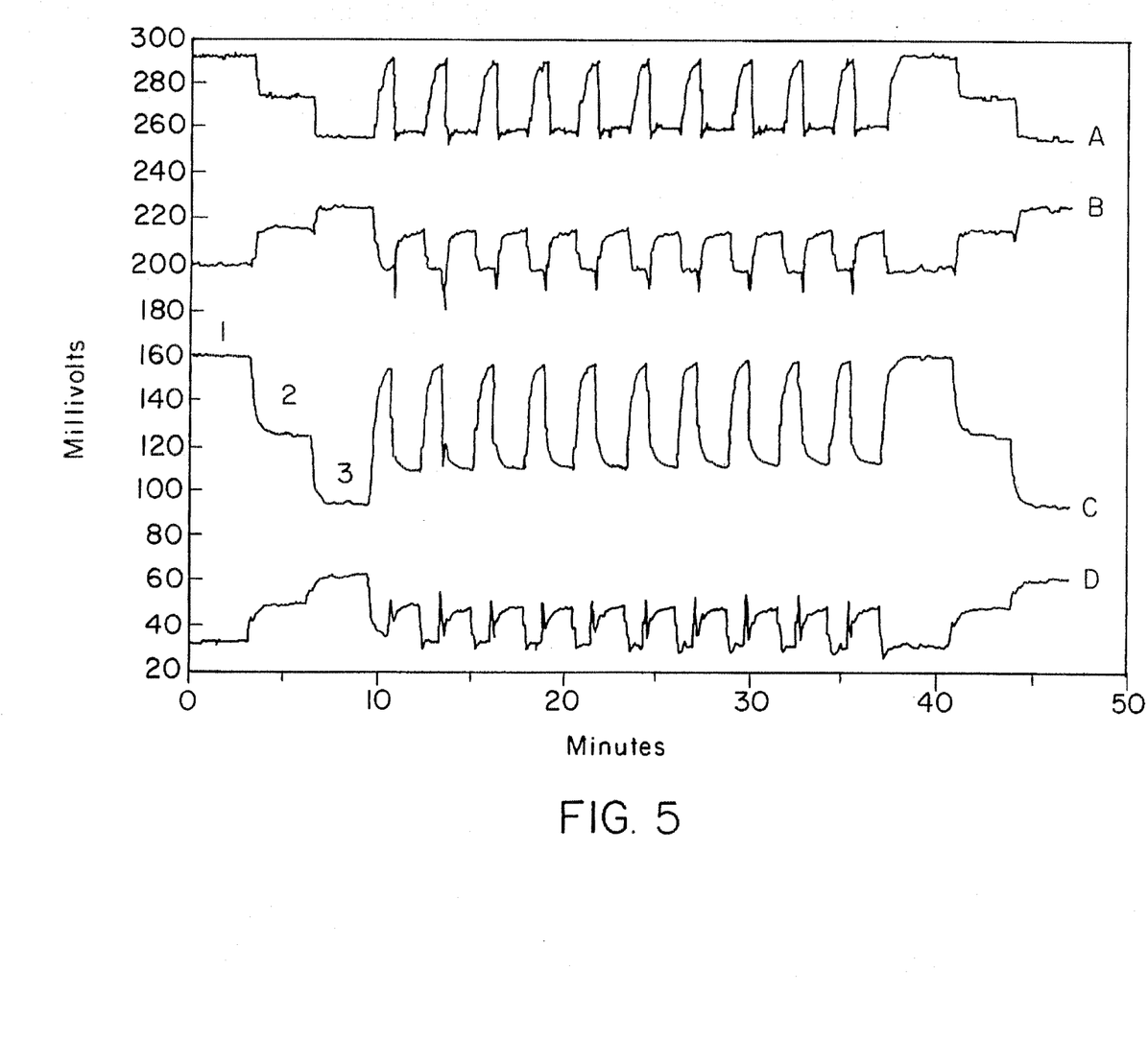
FIG. 5 is a graphical representation of data shown in Example 2, where A is the output of a three-dimensional pH electrode and reference electrode; B is the output of a three-dimensional Severinghaus $pCO_2$ sensor; C is the output of the inventive bicarbonate sensor in combination with a reference electrode; and D is the calculated output of the bicarbonate sensor output subtracted from the pH sensor output.

As shown in FIG. 5, the sensors were first exposed to a three-point calibration in $CO_2$ tonometered bicarbonate solutions, ionic strength adjusted to 0.16 M with NaCl, enumerated in FIG. 5 as points 1, 2 and 3. After the three point calibration, a wash was pulled past the sensors and then a untreated human whole blood sample was measured. This was repeated ten times and the run was ended with a three-point calibration. FIG. 5 provides a display of the responses of the sensors, where A is the output of the pH electrode and reference electrode combination; B is the output of the Severinghaus $pCO_2$ sensor; C is the output of the inventive planar bicarbonate sensor in combination with the reference; and D is resultant ($DpCO_2$) of A output minus C output. The following calibration data was obtained for each output using the first three points.

TABLE I

Response to a Three-Point Calibration in $CO_2$ Tonometered Bicarbonate Solutions

| pH SENSOR | pH | mV vs. ref. | Slope mv/dec |
|---|---|---|---|
| | 7.467 | 257.889 | |
| | 7.163 | 275.908 | −59.60 |
| | 6.860 | 294.068 | |
| $pCO_2$ SENSOR | $pCO_2$ mmHg | mV | Slope mV/dec |
| | 61.746 | 28.745 | 56.28 |
| | 38.003 | 16.435 | |
| | 18.966 | −0.155 | |
| PLANAR | $HCO_3^-$ mM | mV vs ref. | Slope mV/dec |
| $HCO_3^-$ SENSOR | 43.57 | 67.400 | |
| | 13.44 | 97.676 | −59.25 |
| | 3.36 | 133.336 | |
| CALCULATED | $pCO_2$ mmHg | mV | Slope mV/dec |
| $DpCO_2$ | 61.746 | 190.489 | |
| | 38.003 | 178.232 | 58.04 |
| | 18.966 | 160.732 | |

The accuracy of the planar bicarbonate sensor may be checked using the Henderson-Hasselbach equation and the measured values for the pH and the $pCO_2$ of the sample. This technique may also conveniently be used in clinical settings to determine the desired analyte concentration. The pKa used was 6.105. The data found for the 10 replicates for each calibration are as follows.

TABLE II

Values of Planar Bicarbonate Sensors versus the Theoretical Calculated Values

| | MEASURED VALUES | | | CALCULATED VALUES | |
|---|---|---|---|---|---|
| | pH | pCO2 mmHg | $HCO_3^-$ mM | $DpCO_2$ mmHg | $HCO_3^-$ mM |
| mean | 7.39 | 36.4 | 21.4 | 36.3 | 21.0 |
| sd | 0.01 | 0.850 | 0.173 | 0.298 | 0.544 |
| % CV | — | 0.96 | 0.81 | 0.82 | 0.99 |

As shown in TABLE II, the bicarbonate sensor response and the calculated $DpCO_2$ were in good agreement with the theoretical response, as reproducible over the ten replicates.

EXAMPLE 3

Six (6) bicarbonate sensors were constructed as in EXAMPLE 1 except that the cover membrane was prepared using approximately 0.4 wt./vol. % lipophilic salt, a potassium-tetra (p-chloro phenyl borate). The sensors were tested for a test period spanning approximately thirty days coupled to a 200 Series reference electrode. During the test period, each sensor was exposed to 30 human serum samples for approximately one minute daily, thus totaling a testing of approximately 600 serum samples per sensor. During this test period, the sensors were also exposed to a total of 81 human whole blood samples for 2 minutes each in 9 replicates per run, thus totaling approximately testing of 681 protein samples per sensor. Between each protein sample a wash was pulled.

Figure 6:
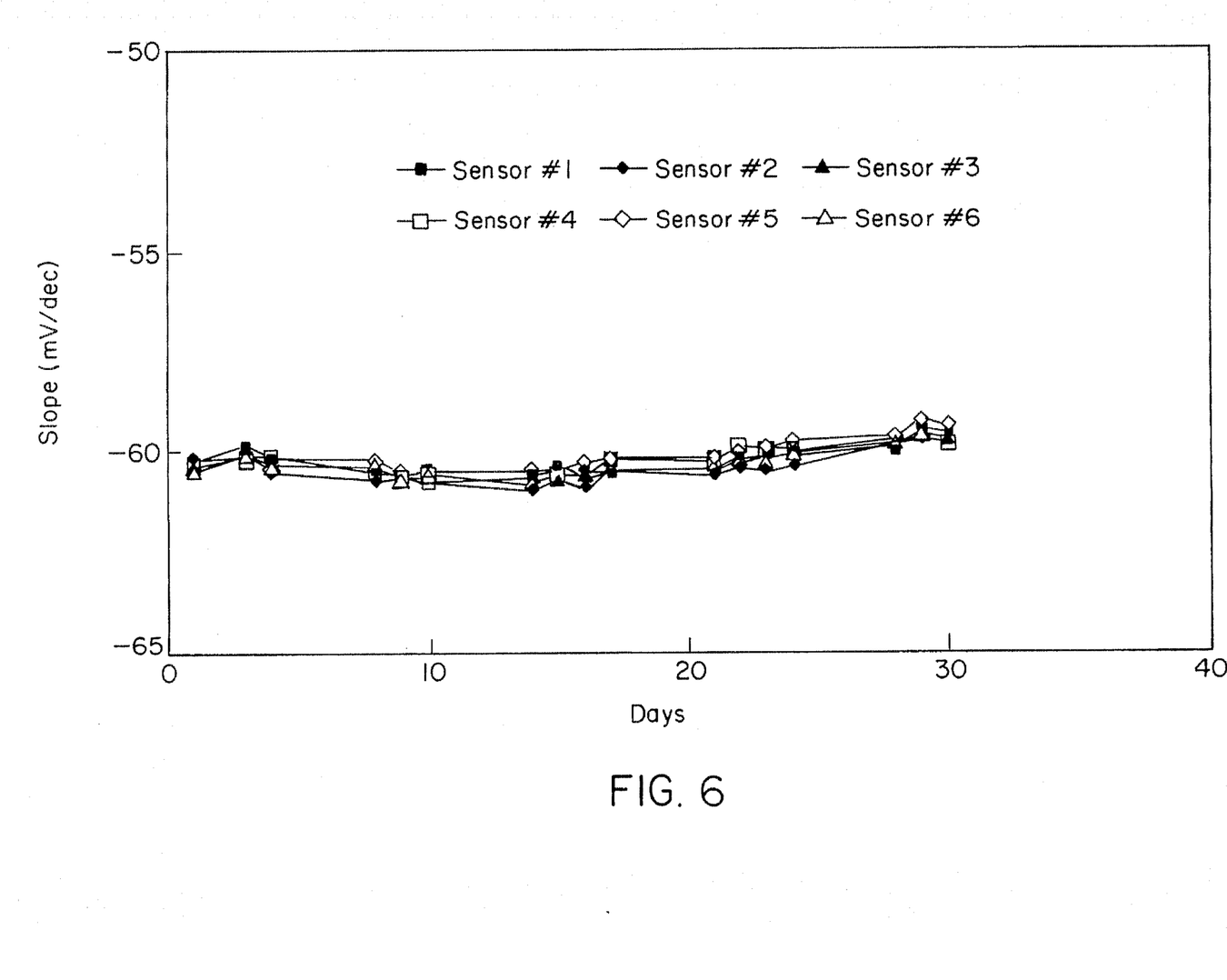
FIG. 6 is a graphical illustration of data from Example 3.

The slopes of the sensors were monitored periodically over the test period using the same calibrators as in EXAMPLE 2. As shown in FIG. 6, over the test period, there is no substantial change in the slope of the sensors. All six sensors maintained a near constant slope of approximately 60 mV/dec for the entire 30 days. This slope agrees well to the theoretical slope.

EXAMPLE 4

Experiments were run using four levels of bicarbonate salt in the internal electrolyte. As shown in TABLE III below, data were collected for eight electrodes prepared as described in EXAMPLE 1 with the exception that the electrodes had varying amounts of sodium bicarbonate ($NaHCO_3$) in the internal electrolyte. SET #1 were prepared with 40 mM (0.0002 M) of the bicarbonate solution; SET #2 were prepared with 60 mM (0.0003 M) of the bicarbonate solution; SET #3 were prepared with 80 mM (0.0004M) of the bicarbonate solution; and SET #4 were prepared with 100 mM (0.0005 M) of the bicarbonate solution. The measurements were conducted on two occasions, DAY 1 and DAY 7, as shown below in TABLE III hereinafter.

TABLE III

Effect of Varying Amounts of Bicarbonate Concentration in Internal Electrolyte

| | Slope mV/dec. SET # 1 | Slope mV/dec. SET # 2 | Slope mV/dec. SET # 3 | Slope mV/dec. SET # 4 |
|---|---|---|---|---|
| DAY 1: | | | | |
| SENSOR 1 | −60.5 | −60.5 | −60.1 | −56.8 |
| SENSOR 2 | −60.4 | −60.5 | −59.9 | −56.9 |
| DAY 7: | | | | |
| SENSOR 1 | −60.2 | −60.5 | −56.6 | −52.4 |
| SENSOR 2 | −59.9 | −60.5 | −55.2 | −50.7 |

As shown in TABLE III, Sets 1 and 2 demonstrated an acceptable stability response at DAY 7.

EXAMPLE 5

Two sets of sensors were constructed as described in EXAMPLE 1 with the exception that the internal electrolyte thickness was varied. Sensor Set A were prepared with a cover membrane of about 48.2 μm and an internal electrolyte residue layer of about 3.4 μm. Sensor Set B were prepared with a cover membrane of about 31.9 μm and an internal electrolyte residue layer of about 4.4 μm. The measured response time was taken at 30 seconds and compared to the response at two minutes for both sets of sensors to provide a % Response at 30 seconds. Results are shown in TABLE IV below.

TABLE IV

Effect of Varying the Thickness of the Internal Electrolyte

| Sensor Set | Cover Membrane | Internal Electrolyte | % Response at 30 Sec. |
|---|---|---|---|
| A | 48.2 μm | 3.4 μm | 95% |
| B | 31.9 μm | 4.4 μm | 90% |

As shown in TABLE IV, Sensor Set A demonstrated a quicker response time, as commercially desirable.

EXAMPLE 6

This example demonstrates that the inventive sensors are capable of reaching a stable potential upon first use when lipophilic salts within a specific range are used in the cover membrane. The lipophilic salt used was a potassium-tetra (p-chloro phenyl) borate. Three sets of sensors were generally constructed as those described in EXAMPLE 1 with the exception that one set contained about 0.7 wt. % lipophilic salt; the second set contained about 0.4 wt. % lipophilic salt; and the third contained about 0.1 wt. % lipophilic salt, with said wt. % based on the total weight of solids present in the cover membrane. The sensors were exposed to an aqueous sample and the potential monitored versus time, with results summarized in TABLE V below.

TABLE V

Effect of the Lipophilic Salt Concentration in Cover Membrane and First Usage Stable Potential

| Lipophilic Salt Concentration | Drift at 1 hour |
| --- | --- |
| 0.7 wt./vol. % | −0.050 mV/min. |
| 0.4 wt./vol. % | −0.013 mV/min. |
| 0.1 wt./vol. % | −0.011 mV/min. |

As shown in TABLE V, the sensors with 0.4% and 0.1% drifted at −0.013 mV/min and −0.011 mV/min. respectively, thus providing better initial stability.

EXAMPLE 7

One hundred (100) sensors were constructed on a 2" by 2" wafer in the format shown in FIGS. 3 (front) and 3a (back). The wafer was printed such that the back contacts were completed first in Au 25 with no dielectric coating. These contacts had present four holes 25a in the alumina with the Au coating inside these holes such that the Au coating of two of the back contacts are connected to the Ag lead 17 on the front side. The front side was then printed (having already been printed with the Ag lead and the Au on the holes) with a dielectric layer leaving only an exposed Ag region 16.

Figure 4:
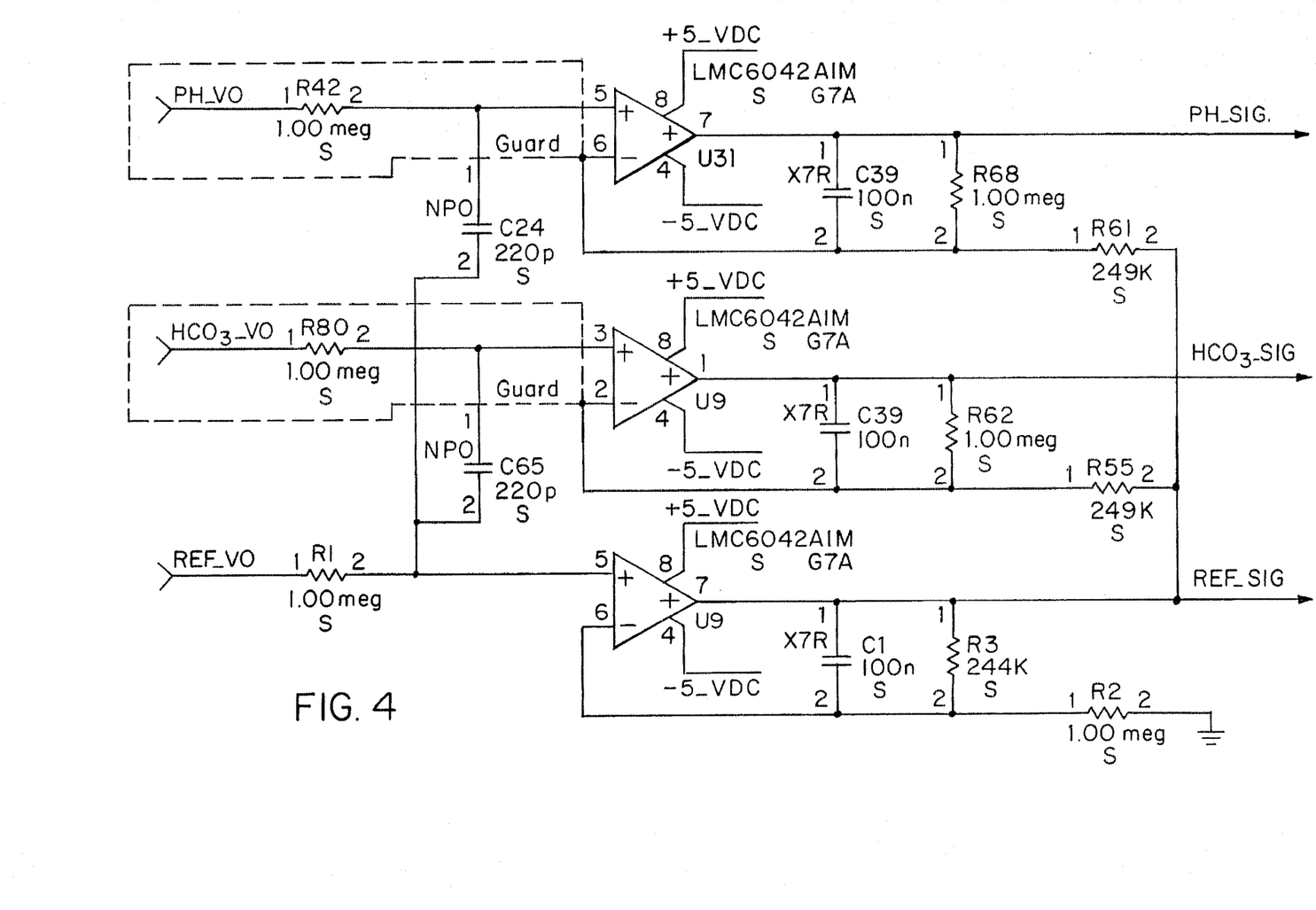
FIG. 4 is the electrical circuitry that may be utilized in obtaining bicarbonate values, pH values, as well as $pCO_2$ values using the inventive sensor.

Three of the sensors were used with the circuitry shown in FIG. 4. These sensors (sensors 1, 2 and 3) were tested along with a glass 200 Series pH electrode, resulting in the following calibration data.

TABLE VI

| | Calibration Data | | |
| --- | --- | --- | --- |
| | Sensor 1 | Sensor 2 | Sensor 3 |
| Bicarbonate Slopes | −58.7 | −58.6 | −59.0 |
| Glass pH Slope: | −57.2 | — | — |
| $pCO_2$ Slope:[1] | 60.4 | 60.1 | 61.2 |

[1] by mathematical substration as previously described

It is not intended that the scope of the claims appended hereinafter are limited to the description as set forth herein, but rather that the claims be construed as encompassing all features of patentable novelty which reside in the present invention, including all features which would be treated as equivalents thereof by those skilled in the art to which the invention pertains.

That which is claimed is:

1. A planar bicarbonate sensor comprising an electrically nonconductive substrate having applied thereto in a planar format an electrically conductive material in at least one region adjacent to said substrate; a dielectric coating covering at least a lead portion of said electrically conductive material but leaving exposed at least an electrode area of said electrically conductive material and leaving exposed at least a contact area on said region of said electrically conductive material; a silver/silver halide transducer present adjacent to said electrically conductive material in said exposed electrode area; an internal electrolyte residue layer present on top of and adjacent to said transducer; a cover membrane present on top of and adjacent to said internal electrolyte residue layer, wherein said internal electrolyte residue layer is an aqueous solution comprised of from about 0.0002 M to about 0.0003 M of a bicarbonate source, and a halide salt of potassium, lithium, or sodium, wherein said internal electrolyte residue layer has been dried.

2. A sensor according to claim 1 wherein said dried internal electrolyte residue layer has a thickness of from about 2.5 μm to about 4 μm and said cover membrane layer has a thickness of from about 20 μm to about 60 μm.

3. A sensor according to claim 2 wherein said cover membrane has a thickness of from 40 μm to 50 μm and comprises a solution of water permeable and gas permeable polymeric material, a proton selective ionophore, a plasticizer, and a lipophilic salt present in an amount ranging from about 0.1 to about 0.5 wt., based on the wt. of the total cover membrane solution.

4. A sensor according to claim 3 wherein said cover membrane has a thickness of about 48.2 μm and is prepared from a tetrahydrofuran based solution comprising from about 1 to about 3 wt. % of a tridodecylamine, from about 25 to about 35 wt. % of a polyvinyl chloride; from about 65 to 75 wt. % of dioctyl phthalate; and from about 0.4 wt. % of a potassium-tetra (p-chloro phenyl) borate.

5. A method of measuring a partial $CO_2$ level in a biological sample, the method comprising contacting a liquid sample with said planar bicarbonate sensor described in claim 1, a reference electrode, and a pH sensor; connecting contact areas of said bicarbonate sensor and said pH sensor with a sensing instrument; connecting said reference electrode with said sensing instrument; providing an electrical current from said sensing instrument through said reference electrode and said contact areas of said sensors; measuring an electrical signal from said bicarbonate sensor to provide a bicarbonate reading on said sensing instrument; measuring an electrical signal from said pH signal from said pH sensor to provide a pH reading on said sensing instrument; and subtracting said bicarbonate reading from said pH reading to provide a $pCO_2$ reading on said instrument.

6. A method of measuring a bicarbonate level in a liquid sample, the method comprising contacting a liquid sample with a planar bicarbonate sensor as described in claim 1 and a reference electrode either directly or indirectly, connecting said exposed contact area of said sensor with a sensing instrument, providing an electrical current from said sensing instrument through said reference electrode and said contact area, and measuring an electrical signal provided by said pH sensing instrument.

7. A method of preparing a bicarbonate sensor, said method comprising selecting a substrate; applying an electrically conductive region on at least a portion of said substrate; coating said electrically conductive region with a dielectric but leaving exposed a transducer region on said electrically conductive region and a contact region on said electrically conductive region; forming a silver/silver halide layer on said transducer region to form a transducer; forming an internal electrolyte dried residue layer having a dried thickness of from about 2.5 μm to about 4 μm thickness on at least said transducer portion of said sensor wherein said internal electrolyte residue layer is prepared from an aqueous solution comprising a bicarbonate source in an amount ranging from about 0.0002 M to about 0.0003 M, and a halide salt of potassium, lithium, sodium; and forming on top of and adjacent to at least said dried internal electrolyte residue layer a cover membrane layer having a thickness of from about 20 to about 60 μm by forming a solution comprising an organic solvent, a gas permeable polymeric or copolymeric material, a proton selective ionophore, a plasticizer, and a lipophilic salt present in an amount ranging form about 0.1 wt. % to about 0.5 wt. %, and then drying said solution to form said cover membrane layer.

* * * * *